United States Patent [19]

Fischel-Ghodsian

[11] Patent Number: 5,071,704
[45] Date of Patent: Dec. 10, 1991

[54] DEVICE FOR CONTROLLED RELEASE OF VAPORS AND SCENTS

[76] Inventor: Fariba Fischel-Ghodsian, 2122 Century Park La., #104, Los Angeles, Calif. 90067

[21] Appl. No.: 537,438

[22] Filed: Jun. 13, 1990

[51] Int. Cl.⁵ ............................................. A61L 15/46
[52] U.S. Cl. ................................. 428/354; 428/905; 424/448; 424/449
[58] Field of Search ............. 424/448, 449; 428/905, 428/343, 354; 523/102

[56] References Cited

U.S. PATENT DOCUMENTS

| | | |
|---|---|---|
| 3,852,416 | 12/1974 | Grubb et al. . |
| 4,031,894 | 6/1977 | Urquhart et al. . |
| 4,047,505 | 9/1977 | McAndless . |
| 4,292,028 | 9/1981 | Barr . |
| 4,379,454 | 4/1983 | Campbell et al. . |
| 4,492,644 | 1/1985 | Matsumoto et al. . |
| 4,597,959 | 7/1986 | Barr . |
| 4,614,787 | 9/1986 | Szycher et al. . |
| 4,638,043 | 1/1987 | Szycher et al. . |
| 4,668,232 | 5/1987 | Cordes et al. .................. 424/448 |
| 4,696,821 | 9/1987 | Belsole ........................... 424/448 |
| 4,720,409 | 1/1988 | Spector ........................ 428/905 X |
| 4,721,064 | 1/1988 | Denk et al. . |
| 4,741,700 | 5/1988 | Barabe . |
| 4,752,477 | 6/1988 | Kraft . |
| 4,797,284 | 1/1989 | Loper et al. .................. 424/448 X |
| 4,803,956 | 2/1989 | Corrigan et al. . |
| 4,824,707 | 4/1989 | Spector . |
| 4,842,761 | 6/1989 | Rutherford . |
| 4,880,690 | 11/1989 | Szycher et al. . |
| 4,911,916 | 3/1990 | Cleary ............................ 424/448 X |
| 4,942,037 | 7/1990 | Bondi et al. ..................... 424/448 |
| 4,943,435 | 7/1990 | Baker et al. .................... 424/448 |

FOREIGN PATENT DOCUMENTS 0305139 3/1989 European Pat. Off. .
2606612 5/1988 France .

OTHER PUBLICATIONS

Evaporative Release of Repellent Chemicals from Porous Polymers, William R. Brade and Timothy D. Davis, Sep.-Oct. 1983, *Cellular Plastics.*

Primary Examiner—George F. Lesmes
Assistant Examiner—D. R. Zirker
Attorney, Agent, or Firm—Poms, Smith, Lande & Rose

[57] ABSTRACT

A controlled release device useful for the release of vapors or liquids is described. The device is a multilayered laminate consisting of a reservoir layer which incorporates an active compound, such as a perfume or fragrance or insect repellant, an impermeable membrane layer adjacent the reservoir layer and a diffusion rate limiting membrane layer adjacent the reservoir layer. The device preferably includes an adhesive layer for adhering the device to skin or a surface and an ornamental decorative layer.

3 Claims, 1 Drawing Sheet

DEVICE FOR CONTROLLED RELEASE OF VAPORS AND SCENTS

BACKGROUND OF THE INVENTION

1. Field of the Invention

The present invention relates in general to controlled release devices which are useful for dispensing an active compound from an article to the environment surrounding the article. More particularly, the present invention is directed to vapor emitting devices which form a laminate and provide an continuous release of a vapor at a substantially constant release rate. The present invention also relates to liquid release devices which form a laminate and provide a continuous release of a liquid or a solid dissolved in a liquid at a substantially constant release rate. The invention also relates to methods of preparing the laminates.

2. Description of Related Art

Various devices and compositions designed to release vapors or liquids from a compound or combinations of compounds have been in wide use over the years. For example, air freshener devices which continuously release an aroma into the environment surrounding the device exist in several varied configurations. Such devices range from a simple cardboard or paper structure saturated with air freshener for use in a confined area to elaborate and decorative air fresheners with more complicated aroma release mechanisms.

Air fresheners with a "designer" appearance are available which adhere to surfaces and contain an air freshener compound within the device. The aromatic air freshener vapors are then released into the surrounding environment for a sustained length of time. The design and construction of these air fresheners is such that they release the vapors from the air freshener compounds at a rapid rate when the device is first put into service. As a result, the release rate diminishes significantly after a relatively short period of time. This produces a vapor release time profile where a relatively large amount of the total available air freshener is released in the initial part of the release period and only a small amount released thereafter. In many cases the aroma is too heavy during the initial part of the intended release period and too little or negligible at the end of the release period. Ideally, the release of the air freshener should be constant during the life of the device.

Other similar vapor releasing devices are perfume patches or pads which provide a temporary short term pleasant odor to the environment in the immediate vicinity of the patch or pad. The most prevalent use for these devices is to advertise perfumes to the public dispensing scent samples in the form of perfume patches or pads. The samples customarily consist of the perfume absorbed on a paper type support. They provide a short term release of the perfume's vapors after which the patch or pad is discarded.

U.S. Pat .No. 4,880,690 describes a perfume patch which is a laminate of polyurethane in combination with other layers including an impermeable backing and adhesive layer. The patch incorporates a perfume in the polyurethane layer and is intended to be adhered to the user's skin in areas such as behind the ear. Additionally, the patch may have an added pigment or decorative design on the polyurethane layer which lends some artistic appeal to the laminate.

The above described perfume pads and perfume patches have the same disadvantages as the air freshener release devices. The perfumes have a rapid rate of release during the initial phase of their life and a significantly reduced rate of release in the later stages. In order to prolong the use time of the patches and increase the release rate later in the life of the pad or patch, it is necessary to increase the perfume loading in the device. Increasing the loading of perfume in the device causes an increase in the initial release rate which in turn may cause an unpleasantly high amount of perfume vapor in the environment.

Controlled release devices also find application for the sustained release of breath fresheners. The use of water soluble mints and other suitable agents for controlling breath odor in devices designed to be contained or adhered to portions of the mouth are known in the art. These sustained release devices normally incorporate the active breath freshener in a device which slowly dissolves over a 1 to 4 hour period and releases the freshener as the dissolution proceeds. Breath fresheners which release active compounds in this manner have a relatively high surface area during the initial portion of the release period resulting in a high dose of the active compound. As dissolution of the article continues the surface area substantially decreases and the dose of the breath freshener necessarily decreases as well. This results in a less than desirable amount of freshener in the mouth.

Controlled release devices are used extensively in the pharmaceutical industry to provide therapeutic and diagnostic compounds to patients over periods of time ranging from minutes to days. In particular, skin patches have been used successfully in administering medications transdermally for several hours at a time with just one patch application. In particular, a patch described in U.S. Pat. No. 4,031,894 for delivering the sea sickness medication, scopolamine, is a five layer laminate designed to be attached to the skin behind the user's ear and deliver the drug through the patch's adhesive layer and into the user's circulatory system.

There is a need to provide a controlled release device which will continuously release vapor into the environment at a controlled, and substantially constant rate over the intended life of the controlled release article.

There is also a need to provide a liquid releasing device which will continuously release liquids into a suitable environment at a controlled and substantially constant rate over the intended life of the release article.

SUMMARY OF THE INVENTION

It is a principal object of the present invention to provide a controlled release device which delivers an active compound from the device at a substantially constant rate.

It is an additional object of the present invention to provide a controlled release device which adheres to a surface for the duration of the release period.

It is a further object of the present invention to provide a controlled release device which incorporates a decorative design for its additional use as an ornamental object.

It is a further additional object of the present invention to provide a controlled release device which will controllably deliver vapors or liquids for a period of from one to seventy-two hours.

The present invention accomplishes the above described objectives by providing a controlled release device in the form of a laminate which consists of at least one layer of a diffusion rate limiting membrane placed adjacent a second layer which incorporates the active compound. The controlled release devices of the present invention may be decoratively embellished with ornamental designs without interfering with the release properties. Additionally, the laminate design provides a means of maintaining an adhesive layer which allows the device to adhere to a variety of surfaces for the duration of its active life. The controlled release device of the present invention may be configured in any of a variety of shapes and sizes depending upon the active compound of choice, the environment of its intended use, and the duration of its intended use.

The controlled release devices of the present invention are multilayer laminates with an active compound incorporated in a reservoir layer. The active compound may be any of a number of useful vapor emitting compounds such as perfumes, various fragrances, air fresheners, insecticides, and insect repellents. Additionally, the active compound may be intended for use in its liquid or dissolved form, e.g. breath fresheners. The laminates of the present invention are constructed such that the active compound diffuses from the reservoir layer into a diffusion rate limiting membrane layer where the vapor or liquid is released into the surrounding environment at a substantially constant rate over the intended life of the device. If desired, for applications in which the controlled delivery device is utilized in visible areas, an ornamental or decorative layer may be incorporated for added appeal.

In accordance with the present invention, the controlled release device may be configured with an impermeable backing and an adhesive layer which allows the device to adhere to wall surfaces, skin, clothing, mucosa tissue, and other items without affecting the release properties. Additionally, the adhesive-surface bond remains intact during its period of use without interference from the active compound.

The controlled release devices of the present invention may be formed into a variety of three dimensional structures ranging in thickness from 200 microns to several millimeters and with surface areas of from about 1 cm$^2$ to several 100 cm$^2$. In this manner, the available surface area and the thickness of the reservoir layer may be varied to meet the needs of the application. For most applications, the device configuration will be sized for a 12 to 24 hour release period for a convenient once a day administration. Shorter and longer release periods are also contemplated as being within the scope of the present invention.

Further objects of the controlled delivery devices of the present invention, as well as a better understanding thereof, will become apparent from a consideration of the following detailed explanation of the preferred exemplary embodiments thereof.

DETAILED DESCRIPTION OF THE PREFERRED EMBODIMENT

Figure 1:
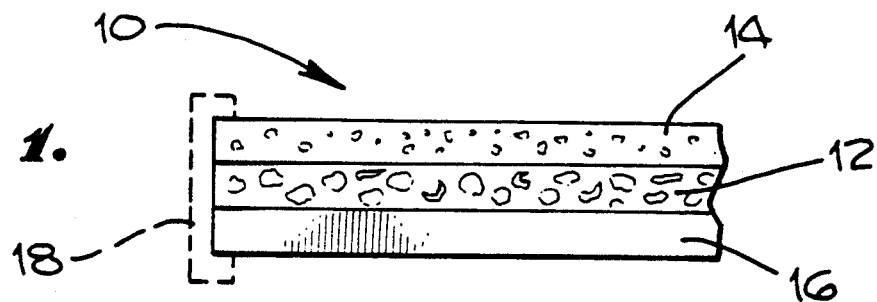
FIG. 1 is an illustration of a controlled release device which forms a laminate comprising a reservoir and a diffusion rate control membrane, and an impermeable backing.

The present invention is a controlled release device in the form of a laminate which may be utilized in any of a number of applications in which it is desirable to release vapors or liquid from an active compound into the environment surrounding the compound. The controlled release device of the present invention provides a substantially constant controlled rate of release of the vapor or liquid from the device. This is accomplished by incorporating a diffusion rate limiting membrane layer into the laminate which controls the rate at which the active compound diffuses to the surface of the device and vaporizes or dissolves into the environment surrounding the device.

An exemplary controlled release device produced in accordance with the teachings of the present invention is shown in FIG. I. The device 10 as shown is a cross-sectional view of a laminate that consists of three layers: a reservoir layer 12 which incorporates an active compound or compounds, a diffusion rate limiting membrane layer 14 adjacent to the reservoir layer, and an impermeable backing layer 16.

In accordance with the present invention the reservoir layer 12 is a porous polymer which is physically and chemically compatible with the active compound or compounds of choice. Suitable polymers include any of a number of foams having cell sizes with a porosity range of from about 0.1 to about 0.8. Appropriate foams are urethane foams, styrene foams, polyvinylchloride foams, polypropylene foams, polyethylene foams, silicone foams and rubber foams. Additionally, polymers which form porous morphologies such as the polypropylene ACCUREL ® manufactured by Armak Co., polyethylene, acrylates, and polyurethanes may be utilized to form the reservoir layer.

The active compound of choice may be incorporated into the reservoir layer polymer by conventional methods known in the art for incorporating polymeric additives. These methods include preforming the polymer foam or the porous polymer or hydrogel and immersing the polymer in the active compound or a solution of active compound for a length of time sufficient to saturate the pores of the polymer. Active compounds may be incorporated with loading levels from about 10% to about 80% by weight of the reservoir.

Alternatively, the active compound of choice may be incorporated in the system utilized to produce the polymer itself, e.g. the monomer or monomers forming the polymer may be dissolved in the active compound and the monomers subsequently polymerized by conventional means to form the polymer. In this manner the vapor emitting compound and the polymer form either a single phase system much like a plasticized polymer, or the active compound and the polymer form a two phase system in which particulates of the compound are dispersed throughout the polymer.

Another embodiment of the reservoir layer of the laminate is in the form of a gelled mixture of a polymer and a liquid. In the case of when the active compound of choice is an oil soluble compound it may be incorporated into a gelled mixture of an oil and polymer. And in the case of when the vapor emitting compound of choice is a water soluble compound it may be incorporated into a gelled mixture of water and a polymer. In applications in which the vapor emitting compound is required at high concentrations within the reservoir layer polymer, the active compound itself can form the liquid portion of the gel without the added oil and water.

As in the case of all polymers which are suitable for use in the reservoir layer of this invention, both the liquid and the polymer which form the gel must be physically and chemically compatible with the active compound. Any gelled mixtures of oil and polymer and gelled mixtures of water and polymer known in the art and suitably compatible and non toxic may be used. Among these gelled mixtures are oil and polyisobutylene, oil and isoprene, oil and silicone, water and polyvinylpyrrolidone, water and hydroxyethylmethacrylate, and combinations including hydroxypropyl cellulose. In addition to diluents and gelling agents, reservoir 12 may include other materials such as stabilizers.

Referring again to FIG. 1, the diffusion rate limiting membrane layer 14 is a thin membrane of from about 10 microns to about 100 microns. It is a microporous polymer which can be selected from any one of the polymers known in the art which is available as a thin microporous membrane with pore sizes ranging from 0.02 microns to about 0.6 microns. Alternatively, it can be a non-porous polymeric membrane which transports the active compound through dissolution in the polymer. Suitable polymers include ethylene vinyl-acetate, polyethylene, polypropylene, polyvinylchloride, cellulose acetate, cellulose nitrate, polyacrylonitrile, and polytetrafluoroethylene.

The diffusion rate limiting membrane 14 is the layer of the laminate that controls the rate at which the vapor or liquid is emitted or released from the active compound which is incorporated into the device. The release rate is a function of the thickness, the porosity, the tortuosity, the concentration gradient of the active compound across the membrane, and the diffusion coefficient of the compound. The active compound diffuses into the micropores of the diffusion rate limiting membrane layer and then is released at a substantially constant rate over the life of the device. This contrasts with the release mechanism of release devices lacking the rate limiting membrane which release very quickly early in their life and release at a significantly slowed rate thereafter.

Impermeable backing layer 16 is a material which does not allow the diffusion of gases and liquids. The backing provides a barrier to the diffusion of the active compound past the edge of the reservoir layer adjacent the impermeable backing layer.

Preferably the vapor and liquid impermeable backing 16 is itself a laminate and consists of a metal foil lined polymer. The polymer may be any polymer which is compatible with the active compound. Suitable candidate polymers include polyethylene terephthalate, high density polyethylene, low density polyethylene, polypropylene, and polyvinylchloride, and polyethylene/aluminized polyester/ethylene vinyl acetate.

For controlled release devices in which the reservoir layer 12 does not provide the necessary "tacky" surface for adhering to the impermeable backing layer 16 and the diffusion rate limiting layer 14, it is desirable to provide a clip or other component for securing the layers of the device together. This component may be a miniature clip, such as the clip shown in phantom at 18 in FIG. 1 which is secured over each face of the device, or a small amount of an adhesive, such as an epoxy, applied to the edges. Alternatively, the laminate layer edges may be secured by heat or solvent sealing techniques. In addition to providing a support system for the layers of the device, the clip 18 or other components prevent the loss of the active component from the edges of the reservoir.

Active compounds which are contemplated within the scope of the present invention include vapor emitting compounds such as perfumes or other fragrances. More particularly, suitable vapor emitting compounds are naturally occurring essential oils, air fresheners, insecticides, and insect repellents. When the reservoir layer of the laminate incorporates one or more of a vapor emitting compound, the compound diffuses to the edge of the reservoir layer and comes into contact with the diffusion rate limiting membrane layer. The vapor emitting compound fills the pores as it diffuses and then is controllably vaporized at a substantially constant rate into the environment surrounding the device.

Additional active compounds also within the scope of the present invention are liquids or dissolved solids such as breath fresheners which are intended to be released into a liquid environment. When incorporated into the reservoir layer of the laminate with a diffusion rate control membrane layer, the liquid diffuses into the micropores of the membrane layer and then becomes solubilized by the liquid environment surrounding the device. When the active compound is a solid which is dissolved in a liquid the diffusions of the solid may be enhanced by prefilling the micropores with the appropriate liquid. In the case of a breath freshener this liquid is water.

The overall size and thickness of the controlled release devices of the present invention depends upon the intended use of the device, the nature of the active compound, and the length of time desired for the device to be in use. In some instances the device may be as thin as 0.02 cm with an area of 4 or 5 cm$^2$. For other applications requiring longer release times with a diffusing vapor emitting compound, the total laminate thickness may be several millimeters thick.

The controlled release device of FIG. i is useful in applications such as releasing insecticide vapors. In particular, pendants intended for use by pet owners as flea and or tick controlling devices may be made from laminates formed by the vapor emitting device. Such flea and tick control devices may be suspended from the animals personal collar and worn by the animal for up to one week and then discarded. The reservoir layer of the vapor emitting devices intended for use as flea and tick control device must be several millimeters thick and 5 to 10 cm$^2$ in area with insecticide contents of from 20% to 60% to provide a sustained and constant supply of insecticide for one week.

Figure 2:
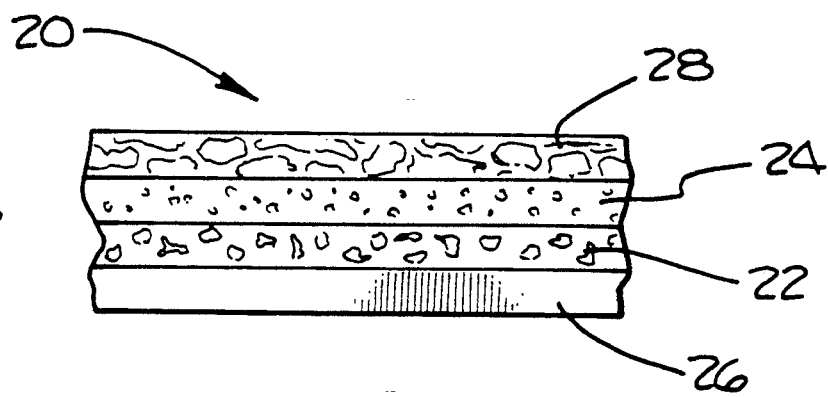
FIG. 2 is an illustration of a controlled release device of FIG. 1 which additionally contains a decorative layer.

FIG. 2 illustrates another embodiment of the present invention. FIG. 2 illustrates a laminate that consists of four layers: a reservoir layer 22, a diffusion rate limiting membrane layer 24, an impermeable backing layer 26, and a decorative layer 28. The reservoir layer 22, rate limiting membrane layer 24, and impermeable backing layer 26 have properties and characteristics as described for FIG. 1. Decorative layer 28 is preferably a thin permeable polymeric material which will readily transmit the active compound and at the same time provide an ornamental quality to the controlled release device.

Useful applications of this decorative device include ornamental "jewelry" type pendants which incorporate a perfume or naturally occurring essential oil fragrance. This device will emit a perfume or fragrance for a period of from 6 hours to 24 hours. Such pendants can be worn for a day and then disposed of after a one time use. The decorative controlled release devices for emitting vapors used in this manner find a particularly advantageous utility by those persons who are allergic to perfumes or have otherwise incompatible skin types for wearing perfumes or fragrances.

Another useful application is a decorative device which incorporates insect repellent material. This device will emit an insect repellent for a period of from about 6 hours to 24 hours. It can be worn on the skin and disposed after a one time use. The advantage of this system is that the insect repellent material is not in contact with the skin, as it is separated by the backing membrane. The insect repellent thus will not be able to penetrate the skin. This eliminates potential health hazards associated with common insect repellent ointments, such as the risk of cancer, and will be particularly beneficial for children.

Also within the scope of the invention as shown in FIG. 2 are decorative controlled release devices used for emitting air fresheners. Such vapor emitting devices may be suspended in an enclosed area where they emit the air freshener at a substantially constant rate over a period of several hours and up to one day in duration.

Figure 3:
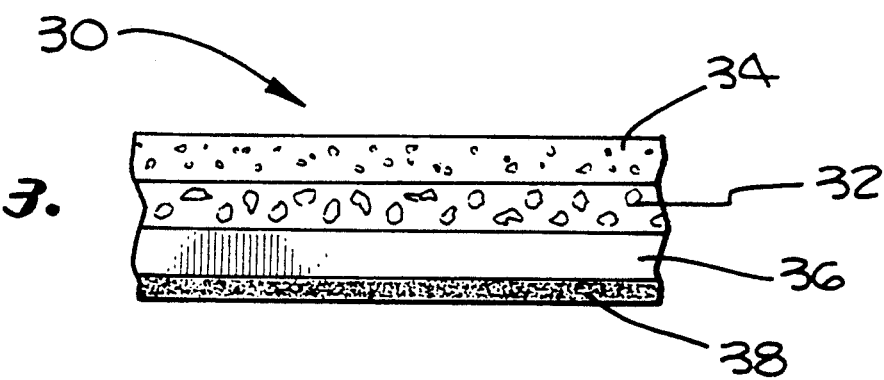
FIG. 3 is an illustration of a controlled release device which has an adhesive layer, an impermeable backing layer, a reservoir layer, and a diffusion rate limiting membrane.

FIG. 3 depicts another embodiment of the present invention, generally designated laminate 30. This preferred embodiment is suitable for adhering to a surface while emitting vapors, liquids, or dissolved solids of choice. In accordance with the teachings of the present invention the features of this embodiment include a diffusion rate limiting membrane 34, a reservoir layer 32, adjacent the diffusion rate limiting membrane layer, a vapor and liquid impermeable backing layer 36 adjacent the diffusion rate limiting membrane layer, and a pressure sensitive contact adhesive layer 38 adjacent the impermeable backing layer.

The diffusion rate limiting membrane 34 has the properties and characteristics as discussed above. The presence of the membrane is necessary for the effective control of the release rate of the active compound from the device. The membrane, as discussed above, is responsible for the substantially constant rate of release of the active compound over the life of the device.

Adjacent the diffusion rate limiting membrane layer 34 is the reservoir layer 32 incorporating the active compound of choice. Reservoir layer 32 may consist of any of the polymeric forms discussed above in the description of FIG. 1. Adjacent the reservoir layer 32 is a vapor and liquid impermeable backing 36. In addition to being a barrier to the active compound, the impermeable backing layer 36 further provides a means to prevent the active compound from interfering with the function of the adhesive as will be discussed below.

Adjacent the vapor and liquid impermeable backing 36 is an adhesive layer 38. The adhesive may be any pressure sensitive contact adhesive suitable for applying to a surface such as the acrylate contact adhesives. When the controlled release device is intended to be used on the skin or any tissue area of a person the contact adhesive must additionally be non-toxic, biocompatible, and hypoallergenic. In particular the biocompatible adhesive may be suitable acrylates, and hydroxypropyl cellulose, medical grade silicone adhesives and their derivatives.

The adhesive is applied to the impermeable backing layer 36 of the laminate. The backing material prevents the diffusing active compound from diffusing into the adhesive layer 38 and diminishing the effectiveness of the adhesive by solubilizing it or destroying the surface-adhesive bond. It is also undesirable for the active compound to diffuse in the direction of the adhesive since the target release point is the environment bound by the diffusion rate limiting membrane 34.

The attendant advantages of the embodiment of the present invention as illustrated in FIG. 3 is the ability of the controlled release device to be conveniently adhered to any surface which will accept the pressure sensitive contact adhesive layer. For example, it is contemplated within the scope of the invention to form a laminate as depicted in FIG. 3 with a reservoir layer 32 which incorporates an air freshener emitting compound and having dimensions of from about 5 cm$^2$ to about 500 cm$^2$ and about 0.2 mm thick. The device may be adhered to the surface of the interior of an automobile or and the wall surface of an interior room. It will effectively release the air freshener over a desired time period at a substantially constant rate.

Also contemplated within the scope of the invention as shown in the embodiment of FIG. 3 are controlled release devices for the release of breath fresheners. The reservoir layer 32 incorporates from 20% to 60% of a water soluble mint or other liquid or solid which is suitable and safe for use as a breath freshener. The device may be adhered to a tooth, the buccal cavity, gum, or palate of a user. Once secured in the user's mouth, the breath freshener is released at a constant rate over a period of time ranging from less than an hour to several hours.

Likewise the self-adhering qualities of the laminate of FIG. 3 are suitable for releasing insecticides from a controlled release device adhered to a pet collar and insect repellents from a laminate adhered to skin or the wall of an enclosed area at a constant rate.

Figure 4:
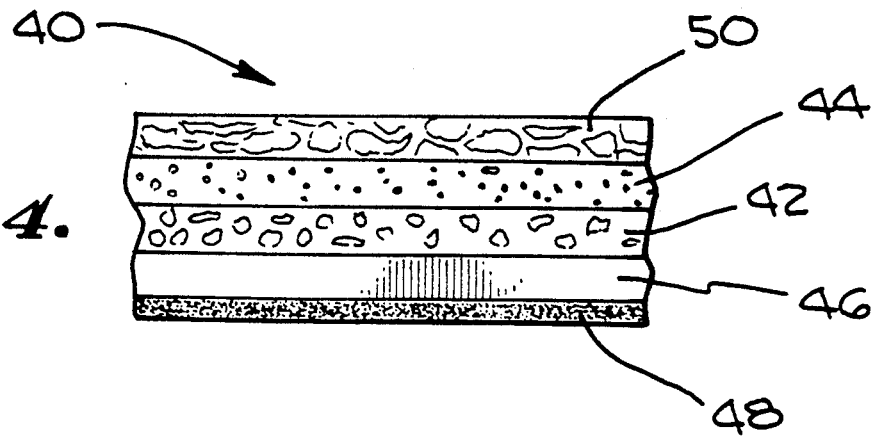
FIG. 4 is an illustration of the controlled release device of FIG. 3 which additionally contains a decorative layer.

A variation of the embodiment of the present invention illustrated in FIG. 3 is detailed in the laminate of FIG. 4. In accordance with FIG. 4 a decorative layer 50 is adjacent the diffusion rate limiting membrane layer 44. A reservoir layer 42 is adjacent both the diffusion rate limiting, membrane layer 44, and an impermeable backing layer 46. An adhesive layer 48 is adjacent the impermeable backing layer 46. The diffusion rate limiting membrane 44, reservoir layer 42, impermeable backing layer 46, and adhesive layer 48 have properties and characteristics as described for FIG. 3. The decorative layer 50 preferably is comprised of a thin highly porous material of polyester base which freely allows the released vapors to diffuse from one surface to the other surface and into the surrounding environment.

A useful application of the laminate pictured in FIG. 4 is a perfume emitting device. The active compound is a vapor emitting perfume and is incorporated into the reservoir layer according to methods known in the art as described above. Further and in accordance with the present invention the perfume emitting device may be decoratively worn by adhering the device to the clothing or the skin of its user. By simply pressing the laminate to clothing or skin, the user has an attractive means to "wear" perfume. The diffusion rate limiting membrane used in combination with the reservoir layer which incorporates the perfume provides a means to effectively and continuously deliver a pleasing aroma at a substantially constant rate for a period of from 6 hours to 24 hours. Persons who prefer to wear perfume but are precluded from doing so because of allergies or skin chemistries are particularly suitable users for the perfume emitting device. Likewise, persons who are drawn to the long lasting scent of perfume on the body or the pleasing appearance of the decorative aspect or the variety afforded by the many different designs which may be available are also potential users.

The following examples are illustrative of the various applications available to those who practice the teachings of the present invention. These examples are not intended to limit the invention in any manner.

EXAMPLE 1

A perfume emitting device comprising the general laminate form shown in FIG. 4 is prepared using the following procedure and materials. An adhesive solution of a medical grade silicone adhesive was prepared by dissolving the silicone adhesive in isopropyl alcohol to a 5% by weight adhesive content. A peeling layer consisting of a standard form release paper was spread in a flat cast vehicle. The 5% solution of adhesive in isopropyl alcohol was then poured onto the peeling layer of standard release paper and the isopropyl alcohol was subsequently allowed to evaporate. The resulting adhesive layer was between 50 to 75 um thick.

After the isopropyl alcohol was evaporated, a gas and liquid impermeable membrane layer consisting of an approximately 50 um membrane of a medium low density polyethylene/aluminized polyester/ethylene vinyl acetate was placed on the adhesive layer. A polymer gel of perfume emitting compound and hydroxypropyl cellulose was then prepared by adding enough of a perfume to powdered hydroxypropyl cellulose to prepare a 50% by weight perfume-polymer gel. The hydroxypropyl cellulose is KLUCEL with a molecular weight of 1,000,000.

The polymer-perfume gel was then spread onto the impermeable membrane layer forming the reservoir layer of the laminate. A diffusion rate limiting membrane consisting of a 40 um thick ethylene vinyl-acetate available from Bertak was then placed adjacent the reservoir layer.

The laminate is topped with a self-adhering decorative layer prepared of porous polyester. For shipping and storage a second peeling layer prepared from any standard release paper which is impermeable to the perfume is placed over the decorative layer.

The final perfume emitting device prepared according to the method described above was a laminate of about 4 cm$^2$ and from 200 to 300 microns thick. The device was safely and conveniently used by peeling the release paper from each face of the laminate and pressing against the user's clothing or skin. In accordance with the provisions of the present invention the laminate releases the pleasant aroma of the perfume at a substantially constant release rate for a period of 16 hours.

EXAMPLE 2

An insect repellent emitting device comprising the general laminate form shown in FIG. 4 is prepared using the following procedure and materials. An adhesive solution of medical grade silicone adhesive layered on a peeling layer is prepared according to the method described in the first paragraph of Example 1.

A gas and liquid impermeable membrane layer consisting of an approximately 50 micron thick membrane layer of a medium low density polyethylene/aluminized polyester/ethylene vinyl acetate is placed on the adhesive layer. A polymer gel of insect repellent emitting compound and hydroxypropyl cellulose is then prepared by adding enough of an insect repellent to powdered hydroxypropyl cellulose to prepare a 50% by weight insect repellent-polymer gel. The hydroxypropyl cellulose is KLUCEL with a molecular weight of 1,000,000.

The polymer-insect repellent gel is then spread onto the impermeable membrane layer forming the reservoir layer of the laminate. A diffusion rate limiting membrane consisting of a 40 micron thick ethylene vinyl-acetate available from Bertak is then placed adjacent the reservoir layer.

The laminate is topped with a self-adhering decorative layer prepared of porous polyester. For shipping and storage a second peeling layer prepared from any standard release paper which is impermeable to the insect-repellent is placed over the decorative layer.

The final insect repellent emitting device prepared according to the method described above is a laminate of about 4 cm$^2$ and from 200 to 300 microns thick. The device is safely and conveniently used by peeling the release paper from each face of the laminate and pressing against the user's clothing or skin. In accordance with the provisions of the present invention the laminate releases the insect repellent without the potentially toxic or carcinogenic insect repellent contacting the user's skin.

EXAMPLE 3

A breath freshener comprising the general laminate shown in FIG. 3 is prepared using the following procedure and materials. An adhesive consisting of a polysacharride type mucoadhesive is spread on a peeling layer of standard form release paper to a thickness of about 100 um. A liquid impermeable membrane layer consisting of an approximate 100 um membrane of aluminized polyethylene terephthalate is placed on the adhesive layer.

A polymer gel comprising about 60% liquid flavoring material, e.g. mint, in a gelled gelatin is prepared by incorporating the mint in the gelatin-water system before it gels and allowing it to gel. The mint-gelatin gel is then spread onto the impermeable membrane layer forming the reservoir layer of the laminate and having a thickness of about 200 um. A diffusion rate limiting membrane consisting of a 50 to 100 um thick porous polytetrafluoroethylene film is then placed adjacent the reservoir layer. The resulting laminate is then cut into squares or circles of 1 to 2 cm$^2$ for use as sustained release breath fresheners. The breath fresheners prepared in accordance with this invention may be adhered to tissue or tooth surfaces in the users mouth and will controllably release the mint at a constant rate over several hours.

EXAMPLE 4

A device useful for the sustained and controlled release of air fresheners comprising the general laminate form shown in FIG. 4 is prepared using the following procedure and materials. An acrylate adhesive is spread on a peeling layer of standard form release paper to a thickness of approximately 75 um. A gas and liquid impermeable membrane layer consisting of an approximately 200 um membrane of a medium low density polyethylene/aluminized polyester/ethylene vinyl acetate is placed on the adhesive layer. An air freshener is incorporated in a 400 um thick layer of ACCUREL porous polypropylene having a 80% void volume by immersing the ACCUREL in the air freshener for three hours. Following the immersion step the ACCUREL is placed on the impermeable membrane layer which is followed by placing a diffusion rate limiting membrane of cellulose nitrate having a pore size of about 0.1 microns. The device is finished with a decorative covering of polyester which provides an added ornamental appeal.

The laminate of Example 3 is cut into sections of approximately 100 cm² and made available for adhering to the walls of kitchens, bathrooms or other environments suitable for using an air freshener. The active compound of this laminate is made available to the environment in vapor form over several days at a constant rate.

Having thus described preferred exemplary embodiments of the present invention, it should be noted by those skilled in the art that the disclosures herein are exemplary only and that alternatives, adaptations and modifications may be made within the scope of the present invention.

I claim:

1. A device useful for the controlled release of a perfume or fragrance, said device forming a laminate comprising:
    a decorative layer consisting of an artistic design formed on a 50 um polyester film;
    a diffusion rate limiting membrane layer adjacent said decorative layer, said diffusion rate limiting membrane consisting of a 40 um thick ethylene vinylacetate film;
    a reservoir layer adjacent said diffusion rate limiting membrane layer, said reservoir layer comprising a gelled mixture of perfume and hydroxypropyl cellulose;
    a vapor and liquid impermeable backing layer adjacent said reservoir layer, said impermeable backing layer consisting of a 50 um thick medium density polyethylene/aluminized polyester/ethylene vinylacetate;
    a pressure sensitive contact adhesive layer adjacent said vapor and liquid impermeable backing layer, said adhesive layer consisting of a medical grade silicone adhesive.

2. The device of claim 1 further comprising one or more clips extending from adjacent said decorative layer to adjacent said adhesive layer.

3. The device of claim 1 further comprising laminate layer edges secured by a sealing technique selected from the group consisting of solvent sealing and heat sealing.

* * * * *